United States Patent [19]
Iwasaki et al.

[11] Patent Number: 4,717,222
[45] Date of Patent: Jan. 5, 1988

[54] OPTICAL SCANNING TYPE SYSTEM

[75] Inventors: Kenji Iwasaki, Utsunomiya; Susumu Shimizu; Hidenosuke Ono, both of Tokyo, all of Japan

[73] Assignee: Kabushiki Kaisha Toshiba, Kawasaki, Japan

[21] Appl. No.: 895,820

[22] Filed: Aug. 12, 1986

[30] Foreign Application Priority Data

Aug. 13, 1985 [JP] Japan .................. 60-179069

[51] Int. Cl.$^4$ .................. G02B 26/08; G02B 5/08
[52] U.S. Cl. .................. 350/6.5; 350/486; 350/626; 350/633
[58] Field of Search .................. 350/6.3, 6.5, 6.6, 486, 350/626, 633, 637, 639, 96.1; 355/66

[56] References Cited

U.S. PATENT DOCUMENTS 3,925,785  12/1975  Firtion et al. .................. 350/6.5

Primary Examiner—John K. Corbin
Assistant Examiner—Vincent J. Lemmo
Attorney, Agent, or Firm—Finnegan, Henderson, Farabow, Garrett & Dunner

[57] ABSTRACT

In an optical scanning type system, a laser beam emitted from a laser generator is directed to a mirror which is fixed on a movable pedestal. The laser beam reflected from the mirror is converged on the end face of one of an array of optical fibers by a convergent lens which is also fixed on the movable pedestal. A cam follower is fixed to the pedestal and caused to contact a cam surface of a cylindrical cam body, which defines a number of steps having a stepwise varying height and formed so as to have a predetermined pitch. The cylindrical cam body is coupled to a step motor. The optical fibers are located so as to arrange the end faces thereof at a pitch corresponding to the pitch of the steps. The cylindrical cam body is stepwisely driven so that the cam follower also stepwisely follows the cam surface. Thus, the pedestal is stepwisely shifted and the laser beam is also stepwisely introduced into the optical fibers.

9 Claims, 7 Drawing Figures

F I G. 2
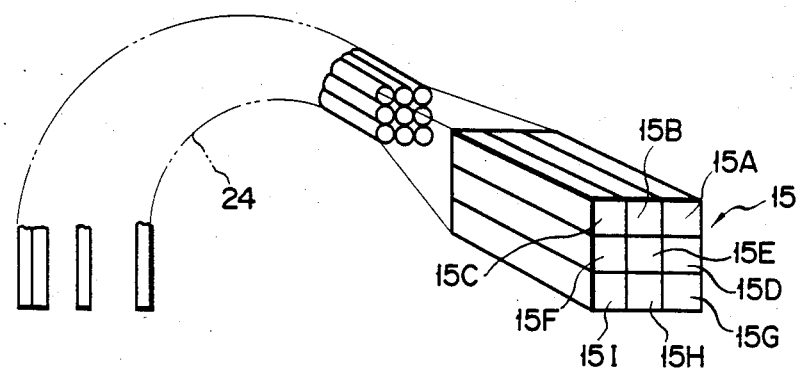
F I G. 3
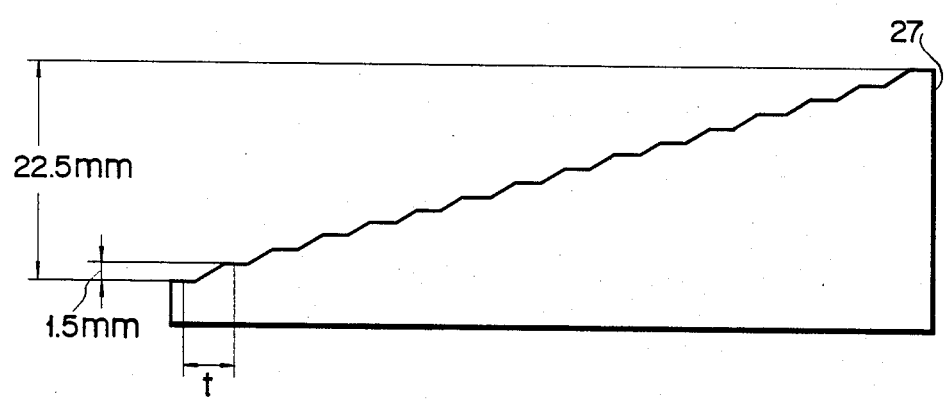

OPTICAL SCANNING TYPE SYSTEM

BACKGROUND OF THE INVENTION

This invention relates to an optical scanning type system for sequentially introducing a light beam into a plurality of optical wave guides, and in particular to an optical scanning type system for directing a laser beam of uniform intensity distribution onto a region of interest of a human subject.

As a light beam type apparatus, use may be made of a laser beam type medical treating device. It has proven effective to direct a ruby laser or argon laser onto a region of interest of a human subject, such as superficial pigmentation.

The energy distribution of a laser beam is, in general, the Gaussian distribution. In this connection it has been found that the mere irradiation of the surface of a living body with a laser beam causes burn spots, an undesirable side effect of medical treatment.

Japanese Patent Application No. 56-27816 discloses the technique of obtaining a laser beam of uniform energy distribution. In this technique, a laser beam is led into a plurality of, for example, glass prisms, where it is totally internally reflected, with the result that the resultant light beam of Gaussian energy distribution emerging from the prism is converted to a light beam of uniform distribution.

However, in this technique a laser beam of high momentary output, such as a pulsed laser beam, can be output from the prism as a laser beam of greater output density, while a laser beam of continuous output, such as an argon laser beam, emerges from the prism as a light beam of smaller output density, so that it takes a longer time to apply a laser beam of the desired energy level to the region of interest of a human subject, such as a superficial pigmentation, in which case sound or healthy living tissue around the pigmentation region will be destroyed due to the heat of the laser beam, thereby causing an undesirable treatment-related problem.

One solution to this problem has been proposed in U.S. Pat. No. 4,534,615, one of whose inventors is Kenji Iwasaki, one of inventors of this application. In this apparatus, a laser beam which is generated from a laser beam generator sequentially enters a plurality of optical fibers having a predetermined array of end faces, then sequentially enters Kaleidoscopes (trade name) bundled in a prismatic array which are coupled to the corresponding optical fibers, and leaves the kaleidoscope bundle. In this case, the laser beam is converted from a light beam of Gaussian energy distribution to a light beam of spatially uniform energy distribution. The laser beam leaving each kaleidoscope has an output density L as given below:

$$L = 4W/S$$

where
  W = the output level of the laser beam generated from the laser beam generator.
  S = the area of the exit end of the respective kaleidoscope.

As will be understood from this equation, if the area of the exit end face of the respective kaleidoscope is constant, then a laser beam of adequate and uniform intensity can be directed to a whole region of the aforementioned kaleidoscope bundle. The laser beam (argon laser beam) generator, taken in combination with the aforementioned apparatus, permits an argon laser to be directed to the region of interest at predetermined density over a broader exposure range.

In order to sequentially introduce a focused laser beam into individual optical fibers in a bundle, a tilting mirror is tilted stepwise by means of a step motor, to cause the laser beam reflected on the tilting mirror to be directed in a fan-shape to permit it to be launched into optical fibers bundled in a linear array. Therefore, there is a risk that a laser beam will not be uniformly introduced into the individual optical fibers due to a variation in the angle of incidence of the laser beam going into the end faces of the individual optical fibers. Since, moreover, the amount of laser beam to be introduced into the respective optical fibers depends upon the uniform rotation of the step motor as well as the tilt angle of the tilting mirror, there is also a risk that a constant amount of laser light will not invariably be introduced into the individual optical fibers.

A solution to this problem is also proposed in the aforementioned U.S. Patent in which, in place of the combination of the tilting mirror and step motor, use is made of a gear mechanism whereby a laser beam focused by a convergent lens after it has been generated from a laser beam generator is linearly moved along a linear array of end faces of bundled optical fibers, to allow it to enter the individual optical fibers. However, there is a possibility that a constant amount of laser light will not invariably be launched into individual optical fibers due to a variation in the pitch of the gear.

The aforementioned U.S. Patent further discloses a system in which the light exit end of the optical fiber, onto which a laser beam is focused by a convergent lens after it has been generated from a laser generator, is moved by a step motor along a rotation locus so that optical fibers arranged along said rotation locus can receive said laser beam in a sequential fashion. However, this method has a drawback, in that a constant amount of laser beam cannot invariably be launched into the individual optical fiber due to the use of the step motor.

SUMMARY OF THE INVENTION

It is accordingly the object of this invention to provide an optical scanning type system assuring that a light beam generated from a light source is accurately time-shared.

According to this invention an optical scanning type system is provided which comprises:
  means for generating a laser beam;
  first reflection means for reflecting the generated laser beam;
  optical means arranged at a predetermined pitch and having a number of light-receiving sections into which the reflected laser beam is introduced; and
  a moving mechanism for moving either one of the first reflection means and optical means stepwise in a specified direction, to allow the reflected laser beam to sequentially enter the respective light-receiving sections of the optical means,
  in which the moving mechanism comprises means for generating a drive force, a cam body having a cam surface defining a number of steps having a varying height, the steps being so formed as to have a pitch corresponding to the pitch of the respective light-receiving section, and a cam follower mechanically coupled to either one of said first reflection means and optical means to allow the cam follower to follow the surface of the cam body.

BRIEF DESCRIPTION OF THE DRAWINGS

FIG. 2 is a perspective view showing an optical system which is optically coupled to the optical fibers in FIG. 1;

FIG. 3 is a diagrammatic expanded view of the cylindrical cam shown in FIG. 1;

DETAILED DESCRIPTION OF THE PREFERRED EMBODIMENT

An optical scanning type system according to one embodiment of this invention will now be explained below with reference to FIG. 1.

Figure 1:
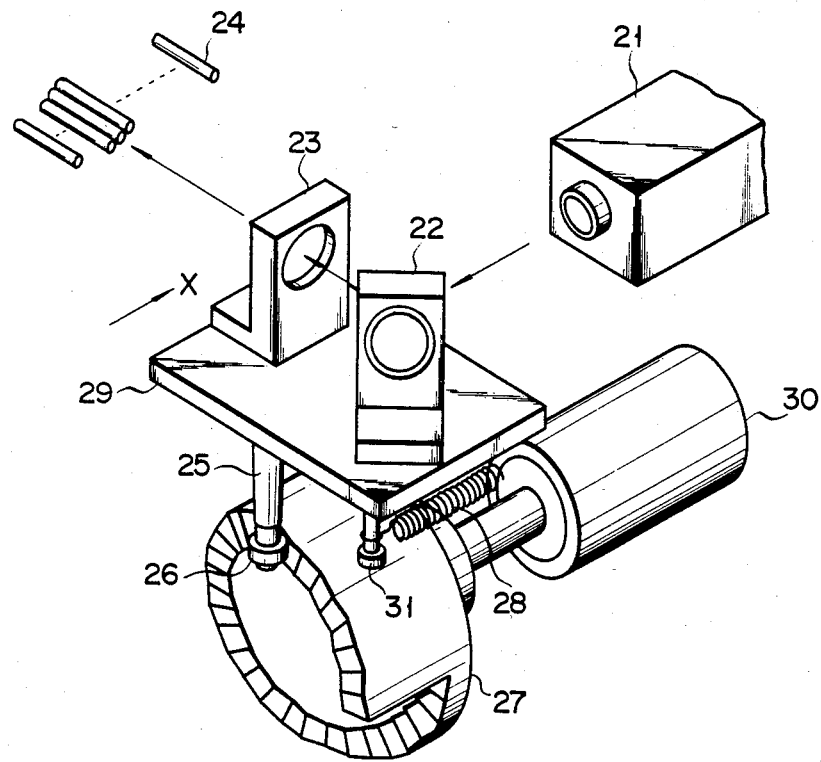
FIG. 1 is a perspective view showing an optical scanning type system according to one embodiment of this invention.

As shown in FIG. 1, pedestal 29 is supported by guides, not shown, such that it can be moved in the direction indicated by an arrow X. Laser generator 21 is so located in direction X as to be spaced apart from pedestal 29, and generates a laser beam in a direction opposite to direction X. Mirror 22 is secured to pedestal 29 such that it is located on the optical axis of laser generator 21, i.e., the optical paths of the beam, in a direction parallel to direction X. Convergent lens 23 is fixed to pedestal 29 such that it is located on an optical path where the laser beam from laser generator 21 is reflected in a direction perpendicular to direction X. Optical fibers 24 are located such that their end faces are arranged in a linear array along the direction X of movement of pedestal 29, and that with the movement of pedestal 29 the axes of the respective optical fibers are individually and temporarily aligned with the axis of convergent lens 23. As a result, the laser beam focused by convergent lens 23 enters the respective optical fiber through the respective end face. As already proposed in U.S. Pat. No. 4,534,615, optical fibers 24 are bundled as a 3-rows×3-columns array as shown, for example, in FIG. 2. This optical fiber array is optically coupled to light transmitting bundle 15 comprised of bundle of glass rods or Kaleidoscope (trade name) 15A to 15I in a 3-rows×3-columns array, for converting the laser beam into one having uniform intensity distribution.

Rod 25 acting as a cam follower is attached at one end to the undersurface of pedestal 29 and at the other end to bearing 26 below the pedestal. Cylindrical cam body 27 having a spiral cam surface is located below the pedestal, and spring 28 is stretched between pin 31 projecting from the undersurface of pedestal and a body portion fixed to the guide, not shown. As a result, bearing 26 is pressed against the cam face of cylindrical cam body 27, to allow it to be smoothly moved along the spiral cam surface of the cylindrical cam body. Where such a smooth movement can be achieved by rod 25 only, then it is not necessary to provide such a bearing.

The cam surface of cylindrical cam body 27 is stepped at an interval of 1.5 mm for each angle of 22.5°, having an external diameter of 60 mm and internal diameter 45 mm, as shown in FIG. 3, so that a stepped, continuous cam surface is provided with each cam step as an inclination face or flat face. A center-to-center distance t of the adjacent cam steps coincides with the center-to-center distance of the adjacent end faces of the optical fibers in the linear array.

Figure 4:
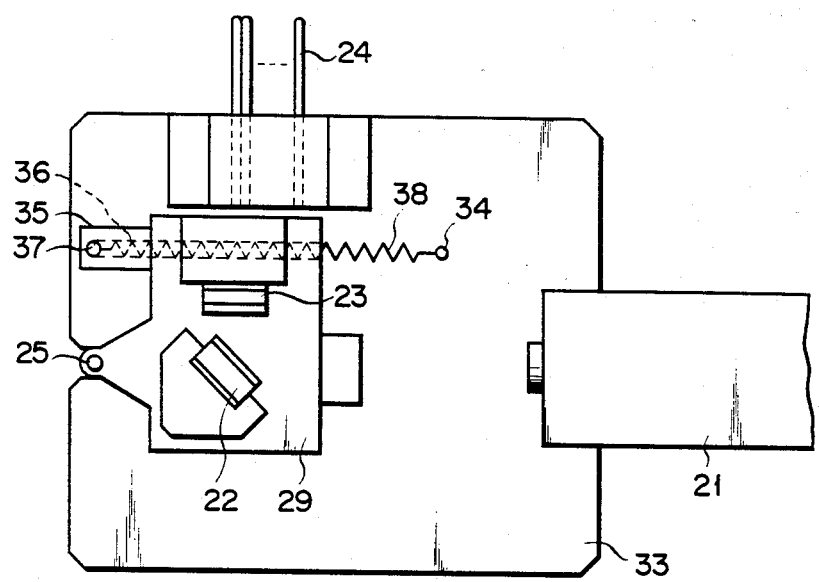
FIGS. 4 and 5 are a plan view and side view, respectively, showing one form of the optical scanning type system of FIG. 1.
Figure 5:
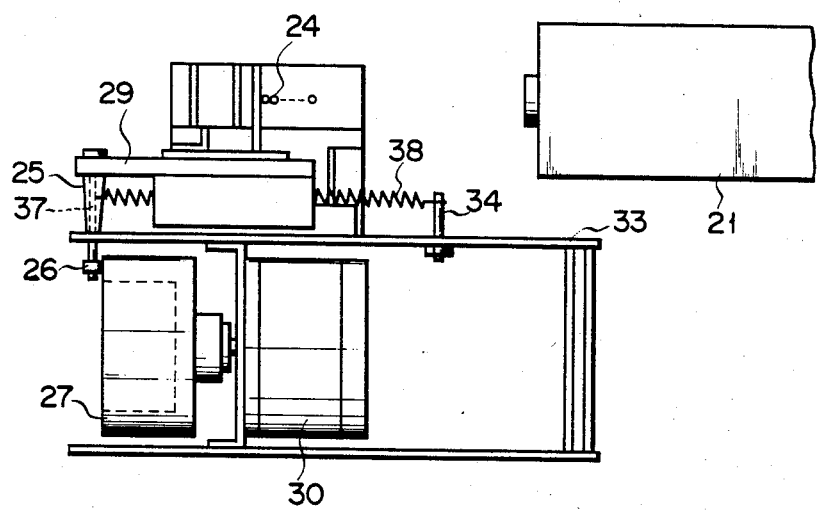

FIGS. 4 and 5 show a detail of the optical scanning type system. In these Figures, the same reference numerals are employed to designate parts or elements corresponding to those shown in FIG. 1 and further explanation is therefore omitted.

In the optical scanning type system shown in FIGS. 4 and 5, pedestal 29 is supported to be movable and step motor 30 is mounted on base plate 33 having upwardly extending pin 34. Horizontal arm 35 is mounted on the pedestal, as shown in FIG. 4, on the same side as that on which rod 25 is mounted. Guide pin 37 is mounted on the free end portion of horizontal arm 35 such that it extends in the same direction as that on which rod 25 extends. Guide pin 37 engages with slide hole 36 in base plate 33. Spring 38 is stretched between guide pin 37 and pin 34 extending up from base plate 33, so that under the influence of spring 38, bearing 26 on the forward end of rod 25 is pressed against the cam surface of the cylindrical cam body.

The operation of the optical scanning type system will now be explained below.

By a command generated from a keyboard, not shown, step motor 30 is rotated at a predetermined time interval. At a time interval of, for example, 0.1 second the cam flat face of cylindrical cam body 27 is rotated to an extent corresponding to a distance t. Needless to say, this rotation time can be set to a predetermined time. When this is done, bearing 26 is stepped from one flat cam face to an adjacent flat cam face, while being maintained in contact with the corresponding flat cam face, so that rod 25 and pedestal 29 are moved in direction X by the amount of 1.5 mm.

After such a stepping movement of rod 25 and thus pedestal 29, a laser beam generation signal is sent from a console to laser generator 21 which in turn delivers a laser beam to mirror 22 over, for example, 0.2 second. This laser beam is perpendicularly bent by mirror 22 and directed to convergent lens 23 where it is focused onto the optical fiber in the optical fiber bundle corresponding to the flat cam surface of cylindrical cam body 27.

By achieving the intermittent rotation of step motor 30 and laser beam emission of laser generator 21 in a proper timing relation, the laser beam can be exactly incident to the corresponding optical fiber of optical fiber bundle 24. In this case, the position at which the laser beam is directed from convergent lens 23 on pedestal 29 onto the corresponding optical fiber in the optical fiber bundle is determined unconditionally. By determining exactly the dimensions of the respective flat cam faces and the respective steps therebetween, the laser beam is moved from one optical fiber to another adjacent optical fiber in accordance with the corresponding step between the adjacent flat faces.

Even if an error occurs, under some circumstances, due to a misalignment of the rotation angle of step motor 30, with a predetermined value, the pedestal can be located to a correct position so long as bearing 26 is located at the flat cam face. Thus, the laser beam is transmitted accurately to the corresponding optical fiber face.

An optical scanning type system according to another form of this invention will be explained below with reference to FIGS. 6 and 7.

Figure 6:
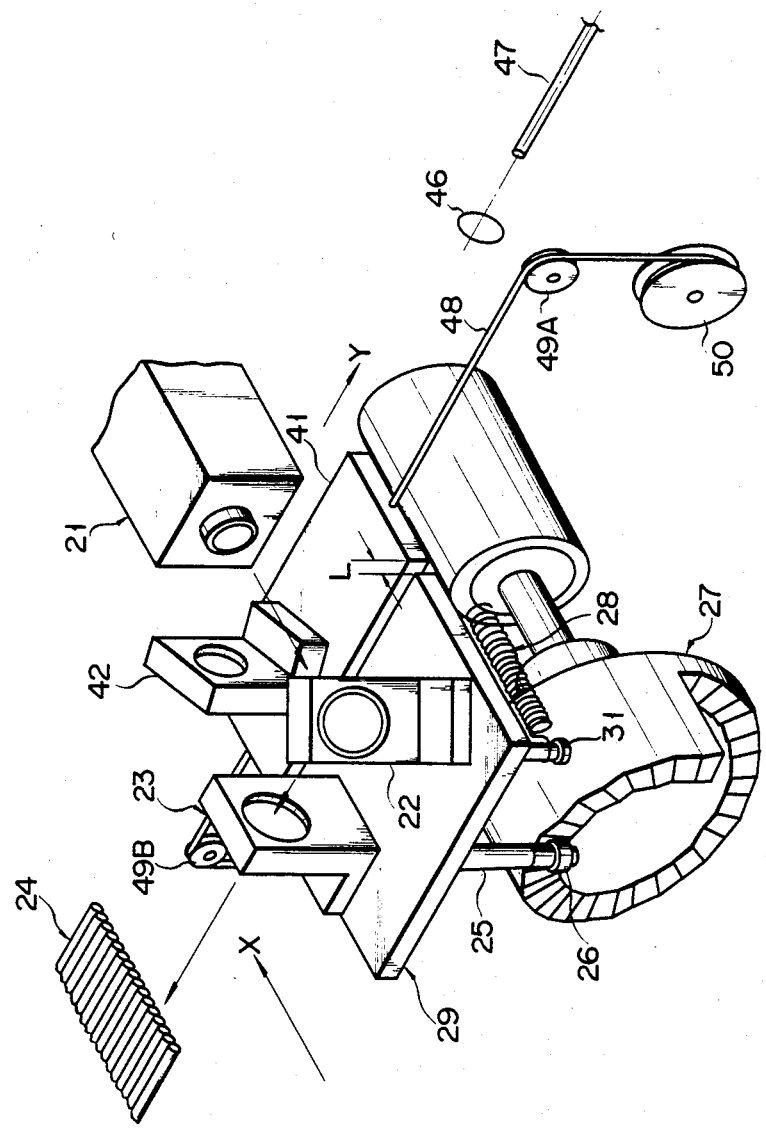
FIGS. 6 and 7 are each a perspective view showing another form of the optical scanning type system of this invention.
Figure 7:
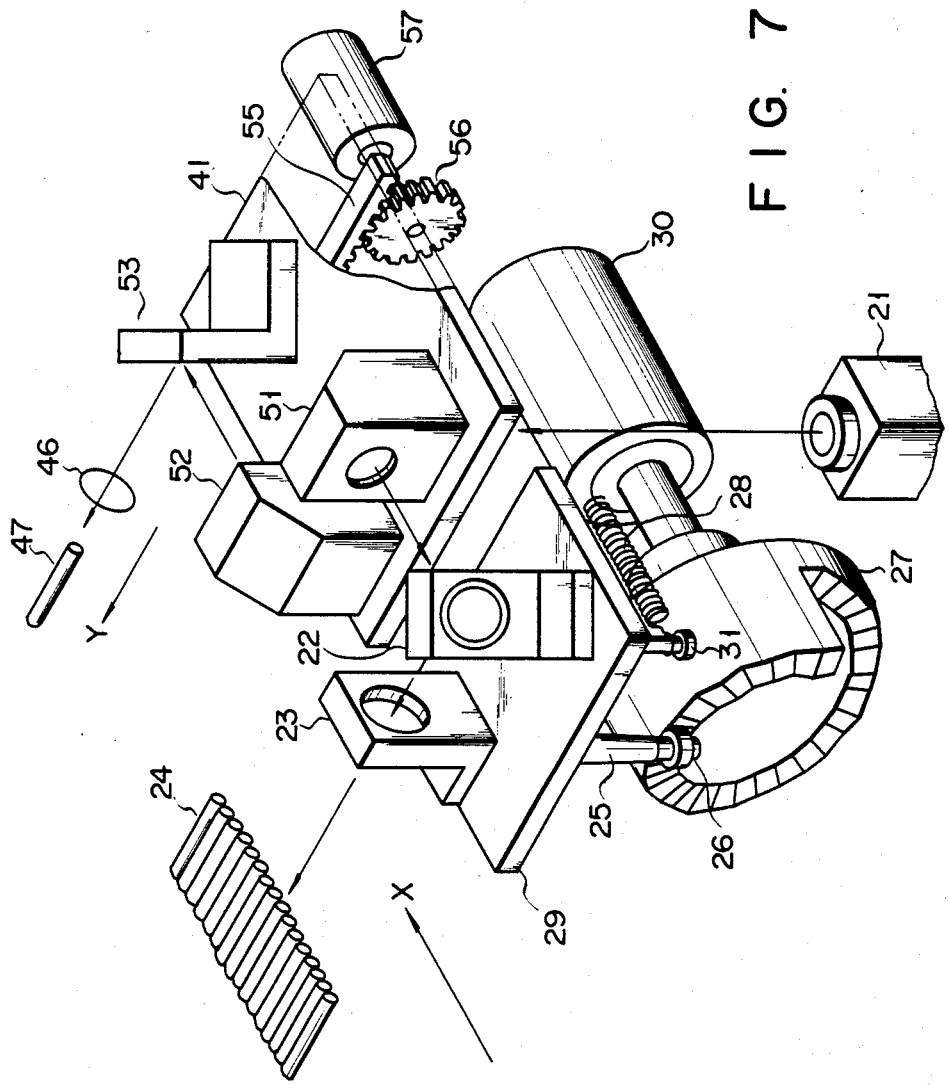

In FIGS. 6 and 7, the same reference numerals are employed to designate components or elements corresponding to those shown in FIG. 1 and, therefore, no further explanation will be necessary.

In this form of the invention, in addition to pedestal 29 another pedestal 41 is also provided which is supported by guides, not shown, so as to be movable in direction Y of FIG. 1. Pedestals 41 and 29 are so arranged that a small gap is created therebetween when pedestal 29 is moved into closest proximity to pedestal 41, and that a distance L exceeding the distance between the highest and the lowest level of the cam face of cylindrical cam body 27 is defined between pedestals 29 and 41 when pedestal 29 is moved away from pedestal 41. Mirror 42 is mounted on pedestal 41 and is located on the optical axis of laser generator 21 when pedestal 41 is shifted to the maximum distance in the direction Y in FIG. 6, so that a laser beam emitted from the laser generator is reflected in the Y direction in FIG. 6. Convergent lens 46 is located on the optical path of a laser beam which is reflected on mirror 42. An optical fiber 47 is located on the optical axis of convergent lens 46 and is coupled to a handpiece type treatment device provided with a laser scalpel. Pedestal 41 is connected to wire 48 which in turn is wound onto take-up wheel 50 through pulleys 49A and 49B.

In the state as shown in FIG. 6, the laser beam is reflected on mirror 22 and introduced into optical fiber 24 through lens 23. When take-up wheel 50 is energized by a motor, not shown, pedestal 41 is pulled by wire 48 in direction Y in FIG. 6. When mirror 42 on pedestal 41 is moved to a position where it is located on the optical axis of laser generator 21, the motor for take-up wheel 50 is deenergized by a stopper mechanism, not shown. As a result, the laser beam which is emitted from laser generator 21 is reflected on mirror 42 and then focused by convergent lens 46 onto optical fiber 47, to allow it to be conducted to the handpiece type treatment device.

In the form as shown in FIG. 7, laser generator 21 is positioned below pedestal 41 having two holes through which a laser beam passes. Above the two holes are located mirrors 51 and 52 which are fixed to pedestal 41. Mirror 22 and lens 23 are located on pedestal 29 along the optical path of the laser beam reflected by mirror 51. A mirror 53 which is mounted on pedestal 41 is situated on the optical path of the laser beam which is reflected on mirror 52. On the optical path of the laser beam reflected from mirror 53, convergent lens 46 and optical fiber 47 are located, as set out above. Pinion 56 is mounted on the undersurface of pedestal 41 such that it is coupled to rack 55 and motor 57. Pedestal 41 is supported by guides, not shown, so that it is movable in the direction Y in FIG. 7.

In the state as shown in FIG. 7, a laser beam which is emitted from the laser generator is reflected on mirrors 51 and 22, and is then launched into optical fiber 24 through lens 23. Upon the energization of motor 57, rack 55 and pinion 56 are driven to cause pedestal 41 to be shifted in direction Y. When mirror 52 on pedestal 41 is moved to a position at which it is located on the optical axis of laser generator 21, motor 57 is deenergized by the stopper mechanism, not shown, and a laser beam emitted from laser generator 21 is reflected on mirrors 52 and 53, and is then focused by convergent lens 46 onto optical fiber 47 and thence to a handpiece type treatment device. It is thus possible to treat a region of interest of a human being by means of the handpiece type treatment device.

Although this invention has been explained in conjunction with the embodiment and variant, it is not restricted thereto. This invention can be changed or modified in a variety of ways without departing from the scope of the invention.

For example, step motor 30 may be rotated always in a predetermined direction. Furthermore, step motor 30 may be sequentially rotated in a normal direction from the flat cam face of the lowest level toward the flat cam face of the highest level, and then in a reverse direction from the flat cam face of the highest level toward the flat cam face of the lowest level, as shown in an expanded view of FIG. 3. Even if this type of driving method is employed in this invention, there is no risk that a backlash will occur as in the conventional system, because of the use made of spring 28 in this invention.

The positional relationship of convergent lens 23 to mirror 22 on pedestal 29 may be reversed. In place of mirror 22, a semiconductor laser element, for example, may be mounted on the position of the mirror, in which case it can be moved directly.

Although, in the aforementioned embodiment, mirror 22 and convergent lens 23 are moved as one unit together with pedestal 29, the optical fiber bundle may be moved relative to this optical system instead.

Furthermore, a predetermined number of optical fibers may be used for a bundle.

A light beam passing through the scanning mirror and convergent lens may be received by a photosenser, such as a photodiode, though this depends upon the use for which this invention is intended. In an object examining device, for example, an array of sample cups containing a blood serum may be located on the light-receiving side of the aforementioned photosenser, so that the absorbance may be examined at high speed.

Furthermore, this invention can also be applied to the field of data transmission, in which case a modulated light beam scans a plurality of right receiving elements at high speed, to permit it to be sequentially transmitted as a train of signals for each element.

According to this invention, members or elements on the light-transmitting side or light-receiving side are moved by a cam mechanism having steps each corresponding to the light scanning pitch, ensuring that light scanning can be performed accurately without being influenced by any backlash and manufacturing errors.

What is claimed is:

1. A system comprising:
   means for generating a laser beam;
   first reflection means for reflecting the laser beam generated;
   optical means arranged at a predetermined pitch and having a number of light-receiving sections into which the reflected laser beam is introduced; and
   a moving mechanism for moving either one of the first reflection means and optical means stepwise in a specified direction, to allow the reflected laser beam to sequentially enter the respective light-receiving sections of the optical means,
   in which the moving mechanism comprises means for generating a drive force, a cam body having a cam surface defining a number of steps and having a stepwise varying height, the steps being formed so as to have a pitch corresponding to the pitch of the respective light-receiving section, and a cam follower mechanically coupled to either one of said first reflection means and optical means, to allow the cam follower to follow the surface of the cam body.

2. A system according to claim 1, in which said cam body is of a cylindrical type having a spiral cam surface at one end.

3. A system according to claim 1, further comprising a pedestal to which said cam follower is fixed, said pedestal supporting said first reflection means.

4. A system according to claim 1, in which said means for generating a drive force is a step motor.

5. A system according to claim 1, in which said light-receiving sections of said optical means are optical fibers.

6. A system according to claim 1, further comprising a bundle of glass rods which are optically coupled to the optical fibers, respectively.

7. A system according to claim 1, in which said first reflection means is moved stepwise by said moving mechanism toward or away from said means for generating a laser beam.

8. A system according to claim 1, further comprising second reflection means for reflecting a laser beam shiftable on an optical path between said first reflection means and said means for generating a laser beam;
    means for shifting said second reflection means; and
    guide means which allows to be guided, a laser beam which is reflected on said second reflection means when said second reflection means is located on said optical path between said first reflection means and said means for generating a laser beam.

9. A system according to claim 8, in which said guide means includes an optical fiber through which a laser beam is transferred.

* * * * *